United States Patent
Mitra et al.

(10) Patent No.: US 12,428,560 B2
(45) Date of Patent: Sep. 30, 2025

(54) HYDROPHILIC CYCLODEXTRIN-CONTAINING SILICONE GELS

(71) Applicant: WACKER CHEMIE AG, Munich (DE)

(72) Inventors: Amitabha Mitra, Adrian, MI (US); Sarah Burke, Milan, MI (US); Feng Wang, Albany, NY (US); Christian Hartman, Dexter, MI (US); Margaret Whitton, Jackson, MI (US); Chelsea Grimm, Perrysburg, OH (US)

(73) Assignee: Wacker Chemie AG, Munich (DE)

( * ) Notice: Subject to any disclaimer, the term of this patent is extended or adjusted under 35 U.S.C. 154(b) by 1012 days.

(21) Appl. No.: 17/419,323

(22) PCT Filed: Dec. 29, 2018

(86) PCT No.: PCT/US2018/068077
§ 371 (c)(1),
(2) Date: Jun. 29, 2021

(87) PCT Pub. No.: WO2020/139403
PCT Pub. Date: Jul. 2, 2020

(65) Prior Publication Data
US 2022/0089873 A1   Mar. 24, 2022

(51) Int. Cl.
C08L 83/06 (2006.01)
C08B 37/16 (2006.01)
C08G 77/12 (2006.01)
C08G 77/20 (2006.01)
(Continued)

(52) U.S. Cl.
CPC .......... *C08L 83/06* (2013.01); *C08B 37/0015* (2013.01); *C08G 77/12* (2013.01); *C08G 77/20* (2013.01); *C08J 3/075* (2013.01); *C08L 5/16* (2013.01); *C08J 2305/16* (2013.01);
(Continued)

(58) Field of Classification Search
CPC ........ C08L 83/06; C08L 5/16; C08B 37/0015; C08G 77/12; C08G 77/20; C08J 3/075
See application file for complete search history.

(56) References Cited

U.S. PATENT DOCUMENTS 3,159,601 A    12/1964   Ashby
3,159,662 A    12/1964   Ashby
3,220,972 A    11/1965   Lamoreaux
(Continued)

FOREIGN PATENT DOCUMENTS

CN    106422428 A    2/2017
DE    19536176 A1    4/1997
(Continued)

OTHER PUBLICATIONS

Eva Moessl et al, "New Silicone Rubbers, 1" Die Angewandte Makromolekulare Chemie (1993) V 205 pp. 185-191.
(Continued)

*Primary Examiner* — Arrie L Reuther
(74) *Attorney, Agent, or Firm* — BROOKS KUSHMAN P.C.

(57) ABSTRACT

Solvent-swollen crosslinked silicone gels containing covalently bonded cyclodextrin groups are prepared by hydrosilylation. The swollen gels are storage stable, compatible with water and polar solvents, and display a significant water break effect.

20 Claims, 2 Drawing Sheets

(51) Int. Cl.
*C08J 3/075* (2006.01)
*C08L 5/16* (2006.01)

(52) U.S. Cl.
CPC ........ *C08J 2383/05* (2013.01); *C08J 2383/07* (2013.01); *C08L 2312/08* (2013.01)

(56) References Cited

U.S. PATENT DOCUMENTS

| | | | |
|---|---|---|---|
| 3,715,334 A | 2/1973 | Karstedt | |
| 3,775,452 A | 11/1973 | Karstedt | |
| 3,814,730 A | 6/1974 | Karstedt | |
| 5,391,592 A | 2/1995 | Herbrechtsmeier | |
| 5,811,487 A | 9/1998 | Schulz, Jr. et al. | |
| 6,043,328 A | 3/2000 | Domschke et al. | |
| 6,365,670 B1* | 4/2002 | Fry | C08L 83/04 514/846 |
| 6,423,322 B1 | 7/2002 | Fry | |
| 6,881,416 B2 | 4/2005 | Fry | |
| 9,358,188 B2 | 6/2016 | Lee | |
| 9,549,894 B2 | 1/2017 | Chiou | |
| 2006/0009592 A1 | 1/2006 | Ochs et al. | |
| 2016/0319079 A1* | 11/2016 | Koellnberger | C08G 77/38 |
| 2017/0369651 A1* | 12/2017 | Cheng | A61P 31/04 |

FOREIGN PATENT DOCUMENTS

| | | |
|---|---|---|
| EP | 3806818 B1 | 11/2021 |
| JP | H06186511 A | 7/1994 |
| WO | 2018228657 A1 | 12/2018 |

OTHER PUBLICATIONS

Dissertation zur Erlangung des Grades "Doktor der Naturwissenschaften" am Fachbereich Chemie und Pharmazie der Johanees Gutenberg—Universitat Mainz, Klaus Wenke, geboren in Mainz, Mainz 1993, 77 pages (part 1).

Dissertation for the degree of "Doctor of Natural Sciences" at the Department of Chemistry and Pharmacy of the Johannes Gutenberg-University Mainz, Klaus Wenke, Born in Mainz, Mainz 1993—English Translation (part 2).

Kazuo Taguchi, Transient Binding Mode of Phenolphthalein-B-Cyclodextrin Complex: An Example of Induced Geometrical Distortion, The Journal of the American Chemical Society, 1986, vol. 108, No. 10, pp. 2705-2709.

M.M. Yin et al., Synthesis of Some Allyl-B-Cyclodextrin Derivatives and their Properties as Capillary GC Stationary Phases, Chromatographia, 2003, vol. 58, pp. 301-305.

Klaus Wenke, Dissertation for the degree of "Doctor of Natural Sciences" at the Department of Chemistry and Pharmacy of the Johannes Gutenberg-University Mainz, Born in Mainz, Mainz 1993.

\* cited by examiner

HYDROPHILIC CYCLODEXTRIN-CONTAINING SILICONE GELS

CROSS-REFERENCE TO RELATED APPLICATIONS

This application is a U.S. National Phase Application of PCT/US2018/068077, filed Dec. 29, 2018, the disclosure of which is hereby incorporated in its entirety by reference herein.

BACKGROUND OF THE INVENTION

1. Field of the Invention

The invention is directed to hydrophilic cyclodextrin-containing, solvent-containing silicone gels, to their preparation, and to their use, particularly in cosmetics and personal care products.

2. Description of the Related Art

Silicone gels may be prepared by numerous methods. Silicone gels have uses, for example, as soft, shock absorbing elastomers. These "gels" are actually very soft elastomers characterized by an extremely low crosslink density. Recently, solvent-swollen silicone gels have been increasingly used in cosmetic and personal care products. For these uses, the silicone gels are prepared in the presence of low viscosity and often volatile silicone fluids, and then subjected to high shear to produce a creamy dispersion or paste, often in combination with a compatible solvent such as a linear or cyclic and often volatile silicone oil, such as decamethylcyclopentasiloxane ("D5").

Silicone gels (also called silicone elastomer gels) provide attractive benefits and properties for cosmetic or personal care product formulation and end use, such a cushiony skin feel, shear thinning behavior of formulations for easy spreading and incorporation of other ingredients, film formation on the skin, thickening of formulations, etc. However, standard silicone gels are hydrophobic and not easily dispersible in water or other polar media such as alcohols or glycerin. Thus, they pose challenges for making stable cosmetic or pharmaceutical formulations, especially if the formulations are water based or contain a large amount of water or other polar solvents. Stable aqueous emulsions of silicone gels are often only possible if a large amount of an emulsifying surfactant is used. Such surfactants are often not well tolerated, and thus their avoidance is desirable.

In order to prepare stable aqueous silicone gel formulation, it has been proposed to employ silicone gels containing hydrophilic covalently bonded polyoxyalkylene groups, particularly polyoxyethylene groups. These latter groups are frequently referred to as "PEG" (polyethylene glycol) groups, even though they may not have any residual terminal hydroxyl groups. The polyoxyalkylene groups may be terminal groups, pendent groups (e.g. bonded to the polymer chain of a silicone (organopolysiloxane)), may be incorporated difunctionally as a part of the polymer chain, or may serve as a link between two polymer chains. Examples of such "polyether silicones" may be found, for example, in U.S. Pat. Nos. 5,811,487 and 6,881,416. Some of these polyether silicones are self-emulsifying in water, while others require the use of surfactants to form stable silicone gel emulsions. These products have experienced some success, for example, in cosmetic formulations.

However, the cosmetics and personal care industries has desired to avoid the use of polyoxyalkylenes, either as units covalently bonded to a polymer, or separately, as non-ionic surfactants. There is a negative perception that such surfactants and related functional groups may contain harmful impurities, and in addition may result in skin irritation. Thus, the industry has long sought a hydrophilic silicone gel which is readily emulsifiable, using only low amounts of surfactants of any type, or no surfactant at all. The industry has also sought silicone gel products which are compatible with water and commonly used polar substances such as alcohols, low molecular weight glycols, and glycerin. Prior silicone gels had limited compatibility or no compatibility with these substances.

Thus, the problem addressed by the present invention is to provide a hydrophilic silicone gel which may be used to form stable emulsions in water and polar solvents, particularly water-soluble or water-miscible solvents. The silicone gels should be able to be prepared in a simple, economical fashion, and preferably should be substantially or totally free of polyoxyalkylene groups.

SUMMARY OF THE INVENTION

It has now been surprisingly and unexpectedly discovered that silicone gels prepared from a reactive cyclodextrin derivative in a hydrosilylation reaction with a component having carbon-carbon aliphatic multiple bonds and an Si—H-functional crosslinker, preferably in the presence of a swelling solvent, are readily emulsifiable in water and other polar solvents, and form stable emulsions. Also surprising is that the cyclodextrin cavity remains useful for "guest/host" complexes, despite being a constituent of a three-dimensional polymer matrix.

DETAILED DESCRIPTION OF THE PREFERRED EMBODIMENTS

Figure 1:
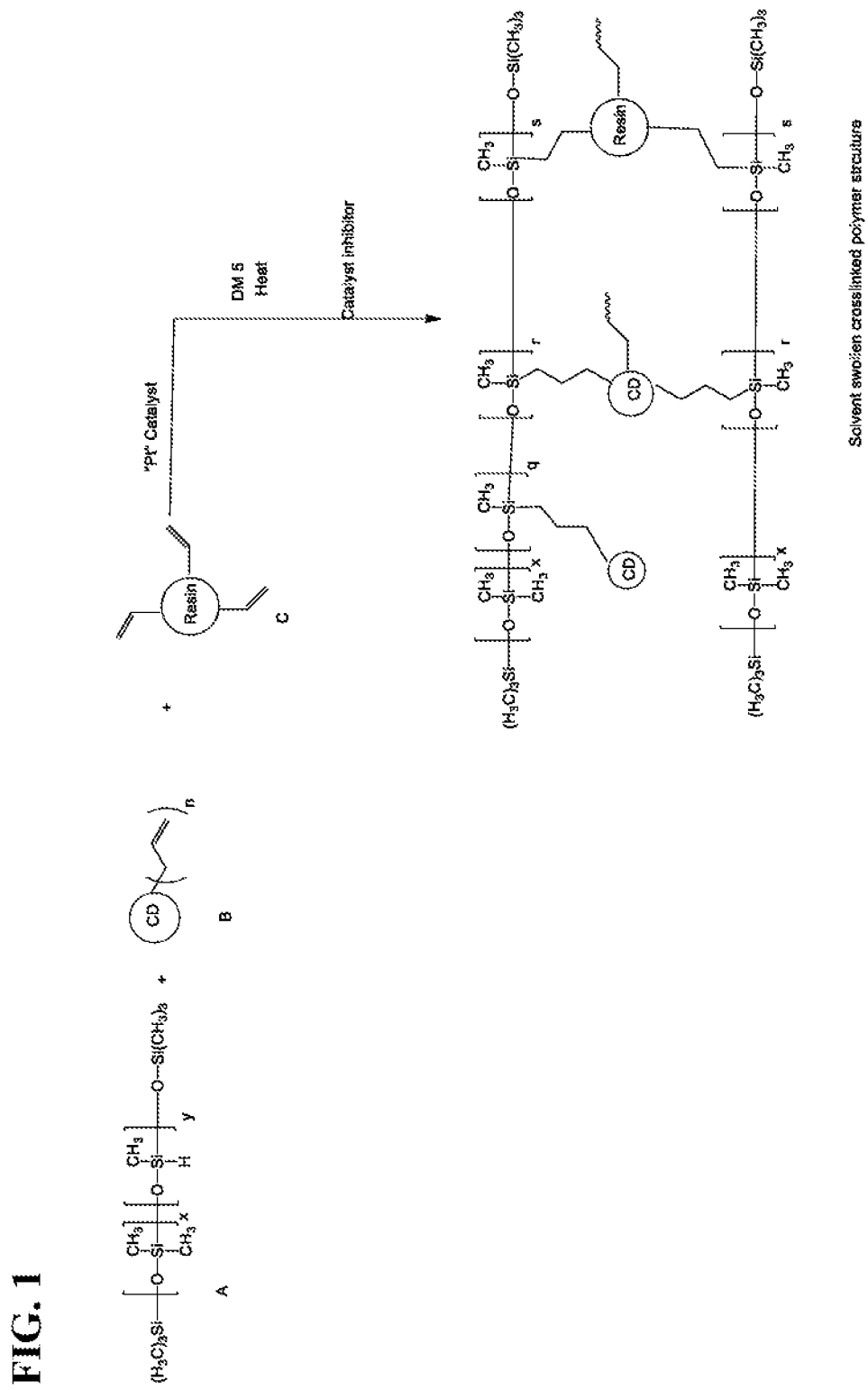
FIG. 1 illustrates schematically one embodiment of gel formation of the invention.

The inventive hydrophilic silicone gels are produced in a hydrosilylation reaction between one or more reactants containing aliphatic unsaturation such as ethylenic or ethylynic unsaturation, and one or more reactants containing Si—H functionality ("silicon-bonded hydrogen."), The reaction is catalyzed by a hydrosilylation catalyst, which may be, for example, a platinum compound or complex. At least one of the reactants must contain a covalently bonded cyclodextrin moiety, for example a cyclodextrin derivative containing ethylenic or ethylynic unsaturation: a silicone (organopolysiloxane) reactant containing hydrosilylation-reaction functionality, to which one or more cyclodextrin groups are covalently bonded; or a silane or silicone bearing silicon bonded hydrogen to which a cyclodextrin moiety is covalently bonded. The reaction preferably takes place in a swelling solvent, and produces a readily disruptable, swollen gel.

Cyclodextrins are cyclic oligosaccharides constructed of w units of α-(1,4)-linked anhydroglucose units, where w is generally from 6-10. The common cyclodextrins contain 6, 7, or 8 anhydroglucose units, and are referred to, respectively, as α-cyclodextrin β-cyclodextrin, and γ-cyclodextrin, often abbreviated as α-CD, β-CD, and γ-CD. Such cyclodextrins and others where w≠6, 7, or 8, are produced by the enzymatic conversion ("digestion") of starch, and are readily commercially available.

Due to their structure, CDs have a hydrophobic interior. Numerous molecules can enter this cavity and form stable complexes, often in stoichiometric ratios, but not always 1:1 ratios. Whether a particular molecule can be a guest molecule in such host/guest complexes is not always predictable, but depends upon the molecular structure of the guest molecule, its physical size, presence or absence of polar groups, etc. The cavity size of CDs increases from α to γ, and larger molecules are generally more easily complexed by the CDs with larger cavities and vice versa. The complexes formed are reversible, in that the guest molecules may often be "liberated" quite easily, and it has been found that some molecules which are notoriously thermally or oxidatively sensitive, curcumin and fish oils being examples, are rendered much more stable by being incorporated into cyclodextrin complexes.

The solubility of cyclodextrins in water is limited, and with respect to the most common cyclodextrins, α-CD, β-CD, and γ-CD, ranges from 18 mg/ml for β-CD to 232 mg/ml for γ-CD. Thus, CDs are much less soluble in water and polar solvents than other saccharides and oligosaccharides. Taking the low aqueous solubilities and hydrophobic cavities into account, it was highly surprising and unexpected that by incorporating CDs into a silicone gel, hydrophilic silicone gels could be produced.

The hydrophilic cyclodextrin-containing silicone gels of the present invention are prepared by incorporating cyclodextrin moieties into the gel through a hydrosilylation reaction. There are three preferable methods of accomplishing this. In a first method, a cyclodextrin (which may be a mixture of cyclodextrins) is modified to contain at least one aliphatically unsaturated group such as one containing ethylenic or ethylynic saturation (component (A)). On average, the cyclodextrin can contain from 1 to 24 carbon-carbon multiple bonds, preferably 1 to 16 carbon-carbon multiple bonds, more preferably 1 to 8 carbon-carbon multiple bonds, even more preferably 1 to 3 carbon-carbon multiple bonds, still more preferably 1 to 2 carbon-carbon multiple bonds, yet more preferably from 1 to 2 or less than 2 multiple bonds, and most preferably, 1 carbon-carbon multiple bond.

The organic groups which contain the carbon-carbon multiple bonds may be, and preferably are, simple alkenyl groups linked to the CDs by an ether linkage, may be a (meth)acrylate group, a maleate or fumarate group, or the like. Such groups may be covalently bound to one of the CD hydroxyl oxygens through any suitable linking group, such as but not limited to, ether, ester, urethane, and urea groups. The remaining unreacted CD hydroxyl groups may remain as free hydroxyl groups, or may have been derivatized or may be previously or subsequently derivatized with other groups not containing ethylenic or ethylynic unsaturation, such as methyl groups, acetate groups, etc. Derivatized CDs containing such modifying groups and other modifying groups are widely available, and can be used as starting materials to form the CDs containing carbon-carbon multiple bonds.

In the context of the present invention, a "cyclodextrin derivative" is a cyclodextrin which has been derivatized by groups which are, not reactive in a hydrosilylation reaction. Such groups include, but are not limited to groups such as those previously mentioned, e.g. hydrocarbon and hydrocarbonoxy groups containing no aliphatic unsaturation. By a "modified cyclodextrin" herein is meant a cyclodextrin or cyclodextrin derivative which has been modified (functionalized) to contain a group having aliphatic unsaturation which can participate in a hydrosilylation reaction, or to contain a silyl or polyorganosiloxyl group containing silicon-bonded hydrogen.

Methods for introducing groups containing carbon-carbon multiple bonds onto CDs are known or easily formulated by a chemist. For example, the methods disclosed in M. Yin et al. CHROMATOGRAPHIA (2003), Vol. 58, p. 301, may be used. Other methods include esterification of CD hydroxyl groups by means of an unsaturated carboxylic acid chloride, esterification by reacting with an unsaturated carboxylic acid such as (meth)acrylic acid; by esterification by reaction with an unsaturated anhydride such as maleic anhydride or acrylic anhydride; by urethanization by reaction with an unsaturated isocyanate such as vinyl isocyanate, allyl isocyanate, or isocyanatoethyl(meth)acrylate or isocyanatopropyl(meth)acrylate; by reaction with an unsaturated epoxy compound, and by other reactions known to the art. The number of carbon-carbon multiple bond-containing groups of the unsaturated CD (A) is limited by the number of free hydroxyl groups in principle, but may also be limited in practice by steric effects. Of course, the higher the number of aliphatically unsaturated groups, the more derivatizing reagent must be used, resulting in higher cost.

A further method of incorporating CD groups by hydrosilylation is to prepare an organopolysiloxane which is reactive in a hydrosilylation reaction by virtue of the presence of aliphatic unsaturation and/or Si—H functionality as an intermediate product, and which contains one or more covalently bonded CD groups on average. For example, an organopolysiloxane containing Si-vinyl groups or Si—H groups and also containing a species reactive with a CID or with a CD derivative may be reacted with the CD to covalently bond the CD to the organopolysiloxane. For non-derivatized CDs or CDs which have been partially derivatized with non-interfering groups such as alkyl groups or acetyl groups, suitable reactive groups on the organopolysiloxanes include anhydride groups such as those derived from maleic anhydride, succinic anhydride, terephthalic anhydride, and phthalic anhydride groups, and other groups reactive with hydroxyl groups, such as isocyanate or epoxy groups.

If the CD has been derivatized with a group which is reactive in hydrosilylation, e.g. an aliphatically unsaturated group or a group bearing or containing an Si—H group, then an organopolysiloxane bearing complementarily reactive groups in stoichiometric excess can be used. For example, a derivatized CD bearing an aliphatically unsaturated group can be reacted with an organopolysiloxane bearing, for example, four Si—H groups, in a 1:1 mol ratio. The hydrosilylated product will contain, on average, one CD moiety per molecule, and will, on average, contain three unreacted Si—H groups to be subsequently reacted to form the gel.

Preferably, the CDs which will participate in the reaction to form a gel will be CDs which have been derivatized to contain, on average, one or more aliphatically unsaturated groups, or the CD will have been covalently bonded to an organopolysiloxane bearing aliphatically unsaturated groups.

if the CD-containing component is an organopolysiloxane bearing Si—H groups or ethylenically unsaturated groups, then the amount of CD moieties in the final gel product may be limited due to selection of the proper portions of organopolysiloxanes necessary to result in gel formation. With "free" CDs modified to contain an aliphatically unsaturated group, the reaction is simpler, more economical, and the CD content may be varied over an extremely wide range.

The aliphatically unsaturated compound (B) which is used in a hydrosilylation reaction to form the desired hydrophilic, cyclodextrin-containing product, may be a linear, branched, or cyclic, or resinous silicone bearing at least two aliphatically unsaturated groups, preferably a linear or branched silicone or silicone resin, and most preferably a silicone resin. The aliphatically unsaturated groups may be any aliphatically unsaturated groups which are able to participate in a hydrosilylation reaction, such as but not limited to alkynyl groups such as the ethynyl group; alkenyl groups such as the vinyl, allyl, isopropenyl, butenyl, hexenyl, cyclohexenyl, and cyclooctenyl groups; and (meth)acrylate groups. For the alkenyl groups, terminal unsaturation is preferred. Vinyl groups are most preferred. The unsaturated groups may be terminal, chain-pendant, or both terminal and chain pendant groups. Organopolysiloxanes bearing terminal unsaturated groups are preferred.

The Si-bonded organo groups of the aliphatically unsaturated silicones which are not aliphatically unsaturated groups, may be any organo group employed in organopolysiloxanes to date, preferably hydrocarbon groups, including alkyl groups such as methyl, ethyl, propyl, butyl, octyl, decyl, dodecyl, and octadecyl, all of these being optionally substituted by halogens, preferably fluorine or chlorine; aryl groups, optionally substituted, such as phenyl, naphthyl, and anthracyl groups; aralkyl groups such as benzyl and phenylethyl; and alkaryl groups such as tolyl. Suitable substituents for all the above groups include halogen, cyano, and alkoxy groups. The non-aliphatically unsaturated groups may also be silicon-bonded hydroxyl or alkoxy groups, preferably methoxy or ethoxy groups. Methyl groups are most preferred.

Preferred aliphatically unsaturated silicones correspond to those containing M groups and one or more of D, T, and Q groups, defined as follows:

M is a monofunctional siloxy group, preferably a monofunctional siloxy group of one of the formulae $$R_3SiO_{1/2} \text{ or } R_aR'_bSiO_{1/2}$$

where a and b are 0, 1, 2, or 3 and total 3;

D is a difunctional siloxy group, preferably a difunctional siloxy group of one of the formulae $$R_2SiO_{2/2} \text{ or } RR'SiO_{2/2};$$

T is a trifunctional siloxy group, preferably a trifunctional siloxy group of the formulae $$RSiO_{3/2} \text{ or } R'SiO_{3/2}; \text{ and}$$

Q is a tetrafunctional siloxy group $SiO_{4/2}$,
where R is a non-aliphatically unsaturated group, preferably a hydroxyl, alkoxy, or hydrocarbon group, and R' is an aliphatically unsaturated group, preferably a vinyl group, and where b is preferably 1, and wherein at least two R' groups are present, and wherein in some embodiments, R may be a cyclodextrin or cyclodextrin derivative.

When the aliphatically unsaturated silicones are linear, they are composed of D units and 2 M units as terminal groups. When the aliphatically unsaturated silicones are branched, they contain M units as terminal groups, D units, and up to 10 mol percent (based on the total of M, T, and Q units) of T and/or Q units ("lightly branched"), or more than 10 mol percent T and/or Q units, for example 15-30 mol percent T and/or Q units ("heavily branched"). A content of less than 0.1 mol percent of T and/or Q units is considered "linear", or "substantially linear." Often, small amounts of T and Q units are unavoidable, due to the method of preparation.

Cyclic aliphatically unsaturated silicones are composed of D units.

Silicone resins are highly crosslinked, network-like polymers which are usually but not always solid, and are generally soluble in aromatic hydrocarbons such as toluene. These polymers generally contain less than 20 mol percent of D units, in addition to M units, and a large proportion of T, and/or Q units. These resins are generally named in accordance with their predominant monomer units, and thus are T resins, MT resins, MQ resins, MTQ resins, MDT resins, MDQ resins, and MDQT resins. T resins and MQ resins are most common.

In these resins, the aliphatically unsaturated groups are usually contained in M units, but if T or D units are present, may also be included in these moieties. MQ resins are preferred. A variety of silicone resins bearing aliphatically unsaturated hydrocarbon groups are commercially available, and the synthesis of silicone resins is well known to the skilled artisan. It should be noted that the formulae previously given for the silicone resins do not include silicon-bonded alkoxy groups, hydroxyl groups, or chloro groups, all of which may be present, e.g. as an "R" substituent, due to the method of preparation. Some silicone resins in particular, can contain considerable quantities of silicon-bonded hydroxy or alkoxy groups, in addition to the hydrocarbon R groups and aliphatically unsaturated R' groups.

In the preparation of the gel, aliphatically unsaturated hydrocarbons and/or aliphatically unsaturated hydrocarbonoxy compounds may also be used, either alone, or in conjunction with the aliphatically unsaturated organopolysiloxanes previously described. Aliphatically unsaturated hydrocarbons contain ethylenic or ethylynic unsaturation, preferably ethylenic unsaturation, as also do the aliphatically unsaturated hydrocarbonoxy compounds. While mono-unsaturated compounds may be used as structure modifiers, gel formation requires the presence of aliphatically unsaturated hydrocarbons or hydrocarbonoxy compounds containing minimally two aliphatically unsaturated groups.

Examples of suitable aliphatically unsaturated hydrocarbons with two or more unsaturated groups include butadiene, 1,5-hexadiene, 1,7-octadiene, divinylbenzene, trivinylbenzene and the like. Examples of suitable aliphatically unsaturated hydrocarbonoxy compounds include the di(meth)acrylates of diols such as ethylene glycol, 1,2-propanediol, 1,3-propane diol, butylene glycol 1,6-hexanediol, 1,4-cyclohexanediol, and 1,4-cyclohexanedimethanol; di-, tri, and tetra-(meth)acrylates of polyols such as glycerol, trimethylolpropane, and pentaerythritol; and polyesters containing unsaturated groups derived from maleic acid, maleic acid anhydride, or fumaric acid, and other esterifiable unsaturated carboxylic acids.

When used in conjunction with an aliphatically unsaturated organosilicon compound, the amount of aliphatically unsaturated hydrocarbon or hydrocarbonoxy compound, relative to the total weight of aliphatically unsaturated hydrocarbon or hydrocarbonoxy compound and aliphatically unsaturated organopolysiloxanes, is preferably less than, in order of increasing preference, 90%, 80%, 70%, 60%, 50%, 40%, 30%, and 20%. Most preferably, the hydrosilylatable compounds present prior to hydrosilylation to form the gel contain no aliphatically unsaturated hydrocarbon or hydrocarbonoxy compounds, or contain less than 10%, more preferably less than 5% on a weight basis relative to the total weight of aliphatically unsaturated hydrocarbon or hydrocarbonoxy compound and aliphatically unsaturated organopolysiloxanes.

Si—H functional crosslinking agent (C) is a necessary reactant, Any Si—H functional compound can be used, for example, straight chain or branched hydrocarbons containing terminal and/or pendent Si—H functionality. However, Si—H functional component (C) is more preferably an organosilicon compound containing the required Si—H functionality. The organosilicon compounds are generally organopolysiloxanes, and, as was the case with the aliphatically unsaturated reactants (B), may be linear, branched (e.g. lightly, heavily, as previously described), cyclic, or resinous.

The crosslinkers (C), when organosilicon compounds, are also described analogously to components (B), with respect to being comprised of M, D, T, and Q units, except that R' substituents are replaced by H. Preferred crosslinkers (C) are organopolysiloxanes bearing silicon-bonded hydrogen, more preferably linear or lightly branched silicones bearing silicon-bonded hydrogen, either terminally, along the polymer chain, or both terminally and along the polymer chain. The R groups of the organopolysiloxane crosslinkers (C) can be the same as those used in the aliphatically unsaturated reactants (B). The methyl group and the phenyl group are preferred, more preferably the methyl group. Preferred Si—H functional silicones are thus composed of -Me$_2$SiO— and -MeHSiO— (D) repeating units, and Me$_3$SiO— and Me$_3$SiO— terminal (M) units. Crosslinkers (C) with only silicon-bonded hydrogen along the polymer chain are preferred.

In the process of forming the inventive gels, a hydrosilylation catalyst (D) is necessary. Hydrosilylation catalysts are well known and widely available from numerous sources. Preferred hydrosilylation catalysts are platinum compounds such as those disclosed in U.S. Pat. Nos. 3,159,601; 3,115,9662; 3,220,972; 3,715,334; 3,775,452; 3,814,730, and German published application DE 19536176 A1. Due to the very small quantity of the expensive hydrosilylation catalyst which is required, these catalysts are generally supplied in a solvent or diluent, preferably a solvent suitable for use in cosmetic and pharmaceutical formulations. One preferred catalyst is "Catalyst OL," a divinyl-terminated polydimethylsiloxane platinum complex diluted with polydimethylsiloxane, available from Wacker Chemie AG, Munich, Germany. Other platinum catalysts such as the well-known Speier and Karstedt catalysts, as well as platinum compounds such as hexachloroplatinic acid are also suitable, particularly catalysts which can be supplied in aqueous solution or dissolved or dispersed in a cosmetically suitable liquid such as propanediol. The amount of hydrosilylation catalyst is not overly critical, and amounts from less than one part per million to 1000 ppm, preferably 2 ppm to 50 ppm, calculated as elemental platinum and based on the total amount of Si—H-functional organopolysiloxanes and aliphatically unsaturated organopolysiloxane, are useful.

In the formation of the inventive gels, in each case, a single type of a component may be used, or more than one type of component may be used. The terms/phrases "aliphatically unsaturated" and "carbon-carbon multiple bond" are intended to be synonymous. In all formulae, silicon is tetravalent. Unless otherwise indicated, the terms "dispersion" and "emulsion" are also intended to be synonymous.

The gelation reaction preferably takes place in a swelling solvent. In general, all the reactants will be soluble in the swelling solvent, and are generally dissolved in the solvent prior to reaction. By a "swelling solvent" is meant an organopolysiloxane or organic solvent or oil which is liquid at room temperature or is liquefiable at a temperature below 50° C., and which is compatible in the crosslinked organopolysiloxane such that a stable gel composition resistant to phase separation is created. The swollen gel containing the swelling solvent will have a greater volume (swollen) than the silicone elastomer itself without solvent. The change in volume is usually appreciable.

However, a portion of swelling solvent may be added later, but very preferably prior to substantial gelation. Since the gel products of the reaction will frequently be used in cosmetics and other personal care products, it is preferable that the swelling solvents used be cosmetically and/or pharmaceutically acceptable. A wide range of oils are useful and commercially available. Included as suitable oils are cyclic silicones such as octamethylcyclotetrasiloxane (D4) and decamethylcyclopentasiloxane (D5); volatile oligomeric organopolysiloxanes having 2 to about 6 siloxy groups; organopolysiloxane fluids; aliphatic hydrocarbons, preferably of 5 carbon atoms or more, such as pentane, hexane, heptane, octane, dodecane, tetradecane, hexadecane, octadecane and isomers of these, and various petroleum fractions containing such hydrocarbons; cyclic hydrocarbons such as cyclohexane, methylcyclohexane, dimethylcyclohexane; lactones, esters such as ethylacetate, butyl acetate, and hexylacetate, and the corresponding propionates and butyrates; diesters such as alkanol diesters of aliphatic carboxylic acids such as dimethyl sebacate, di(ethylhexyl) adipate, and di(nonyl)cyclohexane dicarboxylate, and carboxylic diesters of glycols, such as diethylene glycol bis (heptanoate), diethylene glycol bis(2-ethylhexanoate) ("2G8"), triethylene glycol bis (2-ethylhexanoate) ("3G8"); aromatic hydrocarbons such as toluene and individual xylenes or mixtures of xylenes; ethers such as t-butylmethylether, diethylether; carbonates such as bis(n-propyl carbonate); natural terpene oils such as limonene, natural fragrance oils such as patchouli, sandalwood; paraffinic oils such as mineral oil; natural ester oils such as di- and triglycerides, e.g. jojoba oil, olive oil, fish oil, sesame oil, sunflower oil, rice bran oil, rape seed oil, and canola oil; and other oily substances such as moderate chain length (4-16C) alcohols and glycols, and pharmaceutical oils such as vitamin E oil. This list is illustrative and non-limiting. Any solvent which can produce a solvent-swollen gel is suitable. The ability to employ oils such as vitamin E oil (α-tocopherol) and oils such as olive oil, coconut oil, etc., gives rise to an interesting manner of incorporating these very useful ingredients into cosmetics and personal care products.

In the hydrophilic, cyclodextrin-containing gels of the present invention, the non-reactive components (other than pigments or fillers), comprising mostly or exclusively swelling solvent, may range from ≥95 weight percent to ≤30 weight percent, more preferably 90 to 35 weight percent, and yet more preferably greater than 40 weight percent, still more preferably greater than 50 weight percent. The components (A), (B), and (C), which react to form a crosslinked silicone, make up the remainder of the gel component of the composition. Thus, the crosslinked silicone may constitute from less than 5 weight percent to about 70% of the final gel composition based on the weights of components (A) through (D), preferably 10-25 weight percent, and most preferably 15-25 weight percent. In these calculations, the amounts of hydrosilylation catalyst (5), catalyst poison (F) and any other ingredients (G) are not considered.

The necessary gel forming ingredients are, depending upon the particular method employed to form the gel, (B), (C), and (D) and sometimes (A). At least one of the reactive ingredients ((A), (B), (C)) must contain a bonded cyclodextrin group. However, it may be advantageous, in certain instances, to also include further ingredients (E) such as but not limited to biocides, preferably cosmetically acceptable biocides, fragrances, dyes, pigments, diluents, and acids or bases to alter the pH of the gel. The gel may also include molecules as guests within the cyclodextrin cavities. These molecules include humectants, vitamins, medicinal substances, sensitive natural oils, and the like; essentially all substances which are useful in CD host/guest complexes. The molecules that are included as guests may be released at a suitable time during the application of the gel at a suitable rate.

The gels are generally prepared by suspending, emulsifying or otherwise dispersing, but preferably dissolving the reactive components in all or a part of the swelling solvent. The catalyst is preferably added after the other ingredients have been mixed together. If all the swelling solvent has not been initially added, it is preferable to add the remainder prior to completion of gelation. However, it is also possible to add a portion or all of the swelling solvent after gelation to form the gel or to further dilute the gel.

The reaction temperature is that of typical elastomer preparation, preferably from room temperature to about 150° C., more preferably 500-100° C., and most preferably from 70-90° C. The particular temperature used may reflect thermal sensitivities of ingredients used. In general, lower temperatures require longer reaction times and/or greater amounts of catalyst, and vice versa. At temperatures in the range of 70-90° C., the reaction generally takes several hours. Since the reaction is exothermic, cooling may in some cases be necessary. The reactants are stirred during the reaction, and generally the initial product is a crumbly transparent, translucent or opaque gel. The initial product may be converted to a uniform, creamy gel by more intense agitation, particularly under conditions of high shear, such as the use of a rotor/stator mixer such as an Ultra-Turrax® mixer. The creamy gel product is stable with respect to separation and is readily incorporated into cosmetics and other personal care products, even those containing significant amounts of water and low molecular weight polar substances such as $C_{1-5}$ alcohols and $C_{2-6}$ diols.

The amounts of reactants (A), (B), and (C) can be varied with respect to each other, as long as a stable, creamy gel is produced. For example, greater amounts of the cyclodextrin-containing component (A) confer greater hydrophilicity and water absorption properties. The amounts of aliphatically unsaturated components, e.g. components (A) (when component (A) is aliphatically unsaturated) and (B) relative to the amount of crosslinker (C) are dependent upon the molecular weight and functionality of the respective components. In general, to achieve crosslinking as opposed to only chain extension, the sum of the average functionality of the aliphatically unsaturated components and the average functionality of the Si—H functional components should be ≥4, preferably ≤5. With the exception of the cyclodextrin component (A), it is desirable that the average functionality of the other reactive components each be greater than 2. If the total average functionality is not high enough, or if the average functionality of components (B) and/or (C) is/are not high enough, then a stable gel cannot be formed due to inadequate crosslinking. The relative amounts are able to be determined by one of ordinary skill in the art. Further guidance may be found in U.S. Pat. Nos. 5,391,592, 5,811, 487, 6,365,670, 6,423,322, and 6,881,416, which are incorporated herein by reference. It should be noted that if the CD component (A) contains more than one aliphatically unsaturated group, then this component may also contribute to crosslinking, and thus the functionalities of components (B) and/or (C) may be reduced. If but one aliphatically unsatu-rated group I) present in the cyclodextrin component (A), then the CD groups will be pendent to the silicone rather than "in-chain" groups.

The solvent swollen hydrophilic silicone gels may be prepared by hydrosilylative crosslinking of only components (B) and (C) by hydrosilylation catalyst (D), with or without the present of swelling solvent, provided that (B) and/or (C) contains at least one covalently bonded cyclodextrin group. The solvent swollen hydrophilic silicone gel composition are also preferably synthesizable from (A), (B), and (C) in the presence of (D), where (B) and/or (C) optionally contain a covalently bonded cyclodextrin group. Most preferably, all covalently bonded cyclodextrin groups are contained in component (A). When component (A) is present, it most preferably has been modified to contain aliphatic unsaturation.

The invention can be further illustrated by way of the following examples, which are non-limiting. In the examples, unless stated otherwise, all parts are by weight, and pressure and temperature are standard or are the temperature and pressure ambient in the conventional laboratory, or a temperature reached upon mixing the ingredients, without additional heating or cooling.

Figure 2:
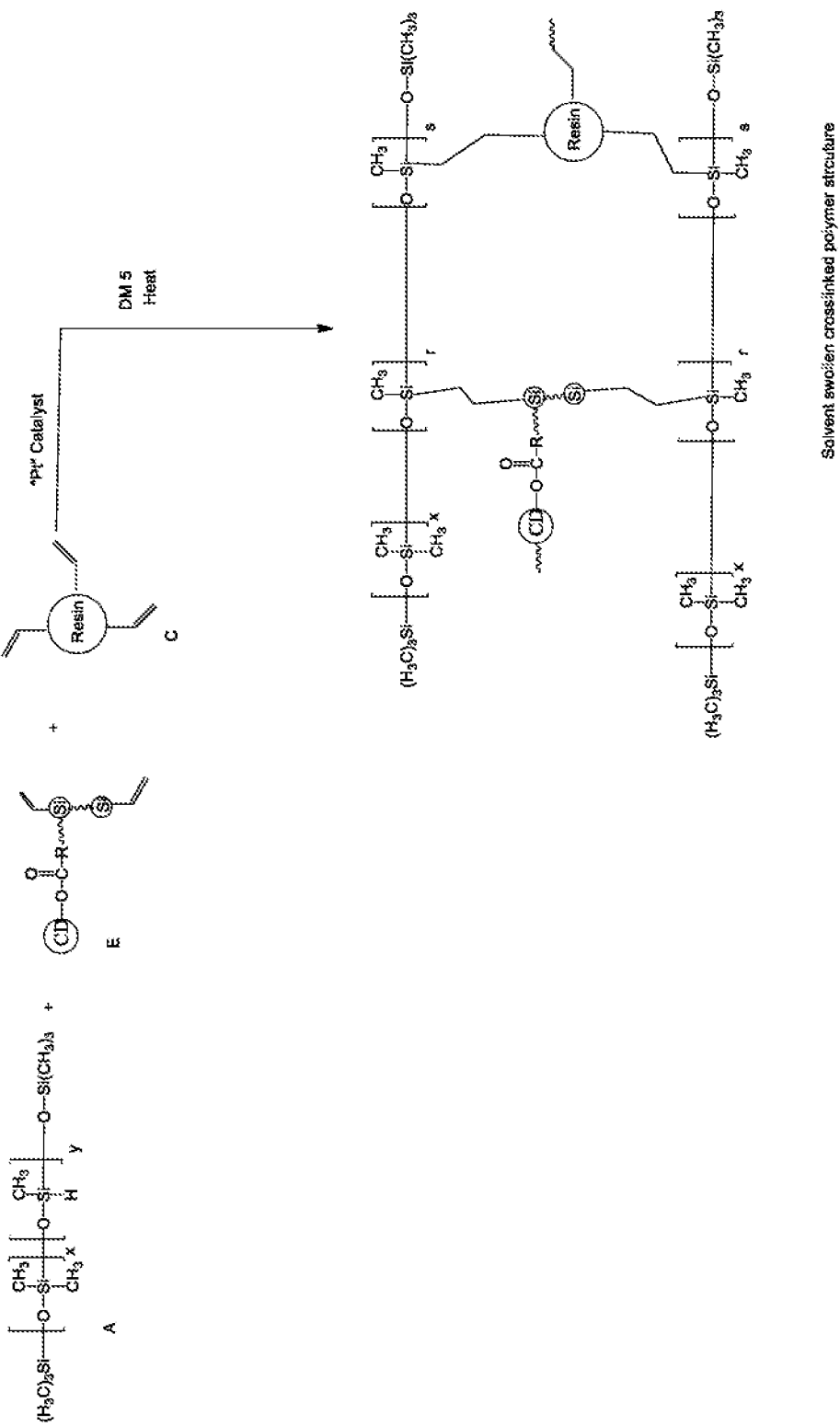
FIG. 2 illustrates schematically a further embodiment of gel formation of the invention.

A simplified schematic illustration of the gelling reaction is presented in FIG. 1, and a further schematic is shown in FIG. 2.

Synthesis Examples

Modification of Cyclodextrin Derivatives:

For examples 1, 2, 3, 4, and 5 and comparative example C6, allyl modified methyl β cyclodextrin was used, which was prepared as follows by modifying methyl β-cyclodextrin CAVASOL® W7 M obtained from Wacker Chemie A.G. For comparative example C7, original CAVASOL® W7 M without allyl modification was used.

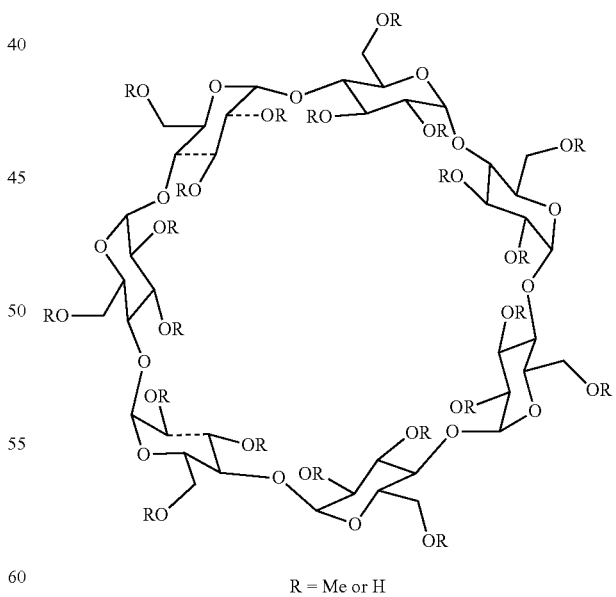

R = Me or H

CAVASOL® W7 M (1.6-1.9 methyl groups on average per glycoside unit)

Synthesis of Allyl Modified Methyl β-Cyclodextrin:

The allyl modified methyl β-cyclodextrin was prepared according to the procedure described in Yin, M., et al.

Chromatographia (2003) Vol. 58 p. 301. The reaction was conducted under continuous nitrogen flow in a three-necked round bottom flask fitted with a condenser and overhead stirrer. CAVASOL® W7 M (40 g, 30.5 mmol) was added to 400 g dimethylsulfoxide (DMSO) and stirred until dissolved. Freshly powdered NaOH (8.55 g, 214 mmol) was added to the solution and stirred for 2 hours at 60° C. The yellowish mixture was cooled to room temperature, allyl bromide (25.9 g, 214 mmol) was added, and the mixture was stirred at room temperature for 1 hour. The mixture was then heated to 60° C. and stirred for 3.5 hours. After cooling to room temperature, the solution was poured into water and extracted with chloroform several times. The combined chloroform layers were washed with saturated sodium bicarbonate solution and brine. The solution was dried over sodium sulfate and dried under vacuum to obtain a yellow sticky solid (15.4 g), The $^1$H NMR and mass spectroscopy confirmed the product to be allyl modified methyl 13 cyclodextrin with a degree of substitution (D.S.) of 0.38 i.e., 0.38 allyl group per glycoside unit.

Vinyl silicone functionalized cyclodextrins VSC-1 and VSC-2 were used for experimental examples 8 and 9, respectively, VSC-1 and VSC-2 were synthesized by reacting CAVASOL® W7 M and an anhydride functional vinyl silicone (from Wacker Chemie A.G.) having the following approximate structure:

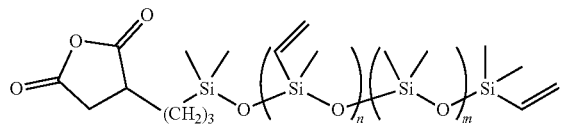

Synthesis of Vinyl Silicone Linked Cyclodextrin Derivative VSC-1:

CAVASOL® W7M 5.0 g (3.82 mmol), dimethyl aminopyridine (DMAP, 0.09 g, 076 mmol) and anhydride functional vinyl silicone (19.8 g) were dissolved in dichloromethane (40 mL) and mixed for 72 hours. Water (20 mL) was added to the mixture, and it was extracted with 20 mL 10% NaHSO4 solution three times. The combined dichloromethane layer was dried over sodium sulfate and the solvent was removed under reduced pressure to obtain a clear highly viscous liquid. $^1$H NMR, IR and MS confirmed the product to be a methyl β-cyclodextrin linked to a vinyl silicone, where on average approximately 0.94 OH groups per glycoside unit are derivatized with the ester linked silicone, iodine number: 74 g iodine/100 g material Synthesis of Vinyl Silicone Linked Cyclodextrin Derivative VSC-2:

CAVASOL® W7M 5.0 g (3.82 mmol), 4-Dimethyl aminopyridine (DMAP, 0.09 g, 0.76 mmol) and anhydride functional silicone were dissolved in dichloromethane (30 mL) and mixed overnight. Water (40 mL) was added to the mixture and it was extracted with 10% NaHSO4 solution three times. The combined dichloromethane layer was dried over sodium sulfate, filtered and the solvent was removed under reduced pressure to obtain a colorless crystalline material, $^1$H NMR, IR and MS confirmed the product to be a modified cyclodextrin linked to a vinyl silicone, where, on average, approximately 0.28 OH groups per glycoside unit are derivatized with the ester linked silicone. Iodine number: 35 g iodine/100 g material.

Synthesis of Silicone Elastomer Gels Based on Allyl Modified Cyclodextrins:

General procedure: A 2000-ml glass reactor is equipped with a condenser, nitrogen inlet, temperature probe, anchor stirrer with wiper attachments, and temperature control system. The reactor is purged with nitrogen, and the reaction is done under continuous nitrogen flow. In the first step, the swelling solvent, modified cyclodextrin derivative (solution in propylene carbonate), the hydrosilylation catalyst and the SiH-functional crosslinking agent are added while stirring at 125 rpm. The mixture is heated in a temperature controlled oil bath to 80 C and mixed at this temperature for 2.5 hours. At this point, the unsaturated organopolysiloxane is added, and the mixture is stirred until the mixture is homogeneous. A second dose of the hydrosilylation catalyst is added, and the reaction mixture is heated at 80° C. with a stirring speed of about 50 rpm. The mixture is stirred at this temperature for 2 hours. Then the catalyst inhibitor is added, and the mixture is mixed at 50 rpm for 15 minutes. The heating is removed and the mixture is cooled to room temperature with stirring at 50 rpm. The mixture is homogenized for 3 minutes at 6000 rpm with an ULTRA-TURRAX® T 25 homogenizer, Compositions for different experiments are described in the Table below:

TABLE 1

| Example | 1 | 2 | 3 | 4 | 5 | Comp. Ex. C6 | Comp. Ex. C7 |
|---|---|---|---|---|---|---|---|
| Swelling Solvent | BELSIL® DM 5[1] | BELSIL® DM 5 | BELSIL® DM 5 | BELSIL® DM 5 | BELSIL® DM 5 | BELSIL® DM 5 | BELSIL® DM 5 |
| Swelling solvent amount (g) | 421.3 | 591.9 | 600.6 | 221.2 | 92.4 | 322.8 | 72.3 |
| Unsaturated silicone resin[2] (g) | 110.3 | 165.9 | 165.5 | 52.4 | 0 | 91.9 | 18.4 |
| Bis-vinyl terminated linear polydimethyl siloxane, Vi-Polymer 1000[3] (g) | 0 | 0 | 0 | 0 | 28.2 | 0 | 0 |
| Si—H containing silicone crosslinking agent[4] (g) | 15.0 | 19.00 | 20.0 | 9.50 | 0.67 | 10.00 | 2.00 |
| Allyl modified CD | 7.71 | 7.99 | 4.18 | 7.95 | 0.34 | 0 | 0 |
| Non-allyl modified CD (post added)[5] | 0 | 0 | 0 | 0 | 0 | 0 | 2.43 |
| Propylene carbonate (g) | 23.13 | 6.00 | 12.54 | 18.05 | 1.03 | 0 | 0 |
| Catalyst [6] (g) (dose 1 + dose 2) | 0.277 + 0.554 | 0.39 + 0.78 | 0.395 + 0.790 | 0.15 + 0.29 | 0.06 + 0.12 | 0.64 | 0.047 + 0.095 |
| Platinum poison[7] (g) | 3.88 | 5.45 | 5.53 | 2.04 | 0.85 | 4.48 | 0.66 |
| Batch size (g) | 582.1 | 791.5 | 809.5 | 311.6 | 123.6 | 429.8 | 95.9 |
| Mol CD- vinyl/mol Si—H | 0.20 | 0.05 | 0.10 | 0.40 | 0.2 | NA | NA |
| Mol Si-vinyl/mol Si—H | 1.12 | 1.33 | 1.26 | 0.84 | 1.12 | 1.40 | 1.40 |
| Mol total vinyl/mol Si—H | 1.32 | 1.38 | 1.36 | 1.24 | 1.32 | 1.40 | 1.40 |

TABLE 1-continued

| Example | 1 | 2 | 3 | 4 | 5 | Comp. Ex. C6 | Comp. Ex. C7 |
|---|---|---|---|---|---|---|---|
| Viscosity (mPa · s) | 65000 | 59000 | 30200 | 15800 | 192000 | 214000 | 164,500 |
| Appearance | Creamy, translucent gel | Creamy, translucent gel | Creamy, translucent gel | Creamy, translucent gel | Creamy, translucent gel | Creamy, translucent gel | Creamy, translucent gel |
| Elastomer (% by weight) in the finished gel[8] | 28 | 25 | 26 | 29 | 25 | 25 | 30 |

[1] Linear 5 cS silicone fluid obtained from Wacker Chemie A.G.;
[2] Ratio $M/M^{Vi}/Q = 7.6/1/11.4$, Mn = 2570, Mw = 5440, iodine number = 18 g iodine/100 g material;
[3] Viscosity = 1000 mm$^2$/s, iodine number = 3.1 g iodine/100 g material;
[4] Poly(methylsiloxane-co-dimethylsiloxane) of approximate formula $M^H(D)_x(D^H)_yM^H$ [0.46% w/w H content, x + y = 140];
[5] CAVASOL ® W7M available from Wacker Chemie AG;
[6] WACKER ® CATALYST OL available from Wacker Chemie AG (1% w/w Pt content);
[7] Polysiloxane having 3-mercapropropyl groups; viscosity 190 mm$^2$/s at 25° C., mercaptan content 0.29% by weight;
[8] % elastomer includes all the components except the diluent, relative to total composition weight.

Synthesis of Silicone Elastomer Gels Based on Vinyl Silicone Modified Cyclodextrins (Examples 8 and 9)

| Example | 8 | 9 |
|---|---|---|
| Swelling solvent (BELSIL ® DM 5)[1] (g) | 274.7 | 167.5 |
| Unsaturated silicone resin [2] (g) | 73.6 | 44.1 |
| Si—H containing silicone cross linking agent[4] (g) | 10 | 6.0 |
| Vinyl Silicone linked CD used | VSC-1 | VSC-2 |
| Vinyl Silicone linked CD amount (g) | 3.21 | 4.04 |
| Isopropanol (g) | 6.42 | 4.00 |
| Catalyst [6] (g) (dose 1 + dose 2) | 0.18 + 0.36 | 0.11 + 0.23 |
| Platinum poison [7] (g) | 2.53 | 1.58 |
| Batch size (g) | 365 | 228 |
| Mol CD-vinyl/mol Si—H | 0.20 | 0.20 |
| Mol resin vinyl/mol Si—H | 1.12 | 1.12 |
| Mol total vinyl/mol Si—H | 1.32 | 1.32 |
| Viscosity (mPa · s) | 119000 | 114000 |
| Appearance | Colorless, translucent, creamy gel | Colorless, translucent, creamy gel |
| Elastomer (% by weight) in the finished gel[8] | 26 | 26 |

General method: A 2000-ml glass reactor is equipped with a condenser, nitrogen inlet, temperature probe, anchor stirrer with wiper attachments, and temperature control system. The reactor is purged with nitrogen, and the reaction is done under continuous nitrogen now. In the first step, the swelling solvent, modified cyclodextrin derivative (50% solution in isopropanol), the hydrosilylation catalyst and the SiH-functional crosslinking agent are added while stirring at 125 rpm. The mixture is heated in a temperature controlled oil bath to 75-80 C and mixed at this temperature for 1 hour. At this point, vinyl MQ resin is added, and the mixture is stirred until the mixture is homogeneous. A second dose of the hydrosilylation catalyst is added, and the reaction mixture is heated at 80° C. with a stirring speed of about 50 rpm. The mixture is stirred at this temperature for 2 hours. Then the catalyst inhibitor is added and the mixture is mixed at 50 rpm for 15 minutes. The heating is removed and the mixture is cooled to room temperature with stirring at 50 rpm. The mixture is homogenized for 3 minutes at 6000 rpm with an ULTRA-TURRAX® T 25 homogenizer. Compositions for two different examples are described in the table below:

Measurement of Water Uptake:

Deionized water solution (dyed with a blue water-soluble dye for better Observation of water droplets) was slowly added with a pipette, a drop at a time, to 20 g elastomer gel, while mixing at 300 rpm with a propeller type overhead stirrer until the mixture would no longer accept additional drops of dyed water. The endpoint was determined by carefully observing whether or not the drop was incorporated into the mixture. If there was some doubt, mixing was stopped and the mixture was examined to determine if there were droplets of free water. The process was assumed to reach end-point when an additional droplet did not incorporate into the mixture even after stirring.

water uptake=(weight of water added to the end-point)×100/weight of gel

TABLE 2

| Sample from Example | Water uptake % |
|---|---|
| 1 | 169 |
| 2 | 148 |
| 3 | 188 |
| 4 | 289 |
| 8 | 40 |
| 9 | 50 |
| C6 | 3 |
| C7 | Blend with water not stable |

Compatibility with Solvents:

The elastomer gels from this invention are compatible with various solvents, such as isopropanol, glycerine, and esters, which are commonly used for cosmetics and other formulations.

Some examples are provided below:

Elastomer gels prepared according to Example 1 and Example 3 were mixed with various solvents either with an overhead stirrer or with a Speedmixer™:

| Elastomer Gel | Solvent | Gel to solvent ratio | Appearance of the blend |
|---|---|---|---|
| Example 2 | Glycerol | 1:1 | Creamy, stable dispersion |
| | | 1:3.7 | Creamy, stable dispersion |
| | Isopropanol | 1:2.0 | Liquid, stable dispersion |
| | Castor oil | 1:1 | Pasty, stable dispersion |

-continued

| Elastomer Gel | Solvent | Gel to solvent ratio | Appearance of the blend |
|---|---|---|---|
| Example 3 | Glycerol | 1:1 | Creamy, stable dispersion |
| | Castor Oil | 1:1 | Gelatinous, stable dispersion |
| | Isopropyl palmitate | 1:1 | Slightly hazy, liquid, stable dispersion |
| | Isopropyl myristate | 1:1 | Slightly hazy, liquid, stable dispersion |

Water-Break Effect:

The "water-break effect," also called "water-release effect" or "quick break effect," is very attractive for providing unique skin fed when a cosmetic product is applied on the skin. This effect is described in U.S. Pat. Nos. 9,358,188 and 9,549,894, which are incorporated herein by reference. The water blends of CD modified gels show water release/water break/quick break effect on rubbing on the skin.

A blend was prepared by mixing 1 part of the elastomer gel prepared according to Example 1 and 1.4 parts of water with an overhead mixer. A creamy mixture was obtained. Approximately 0.2 g of the creamy mixture on rubbing with a forefinger for approximately 20 seconds generated visible droplets of water. Similar observations were made when an elastomer gel prepared according to Example 4 was used to prepare a blend with water.

Application of the Silicone Elastomer Gel for Encapsulation:

The encapsulation ability of cyclodextrin cavity can be determined by the phenolphthalein discoloration test. Phenolphthalein forms a complex with the cyclodextrin cavity because of which the pink color of alkaline phenolphthalein solution disappears (Reference: Kazuo Taguchi *J. Am. Chem. Soc.*, Vol. 108, No. 10, 1986, 2705). To determine if the cavity of the cyclodextrin attached to the crosslinked network is still available for encapsulation the following experiment was performed:

A sample of gel (10 g) prepared according to Example 1 was taken in a small beaker. 3.0 mL of an ethanolic solution (0.01 M) of phenolphthalein with 1 drop of 25% aqueous NaOH was added. The pink color of the alkaline phenolphthalein solution disappeared after few minutes of stirring with a glass rod. For comparison, a similar test with a commercially available hydrophobic silicone elastomer gel BELSIL® REG 1102 (INCI: Dimethicone (and) Dimethicone/Vinyltrimethylsiloxysilicate Crosspolymer) did not show any discoloration.

The bound phenolphthalein can be released (as observed by reappearance of the pink color) by using an aqueous solution of sodium dodecyl sulfate, which indicates that the binding is reversible.

The encapsulation ability of CD modified elastomer gels have practical use for cosmetics and pharmaceutical formulations where the encapsulation of active ingredients (e.g., vitamins, antiaging actives, drugs, etc.) and their release later at a convenient point of application is important. This encapsulation and release ability could also be used in healthcare and woundcare, for example, wound dressings or transdermal drug delivery patches/device containing these types of gels where the gel can incorporate an active and then release in a controlled manner. Another example could be bodily implants incorporating such type of gel where the gel could contain active material for controlled release. Another example could be topical ointments containing the elastomer gel that also contain active materials that gets released at a sustained rate.

Examples of active compounds are: biocides, insecticides, fungicides, herbicides, pheromones, fragrances, flavorings, drugs, pharmaceutical active compounds, active compounds for antistatic finishing or flame retardant finishing, stabilizers (UV), dyestuffs.

The encapsulation ability can be used to selectively absorb undesired materials. The gels thus can also be suitable as separating materials;

Examples of Silicone Elastomer Gels in Cosmetics Formulations:

Example in Skincare Formulation: Cucumber Moisturizing Gel

Cucumber Moisturizing Gel formulations were made with inventive examples 1 (Formulation 1) and 3 (Formulation 2). A comparative formulation (Formulation 3), which does not have any of the elastomer gels, was also made. The formulation compositions are shown in the following table:

TABLE 3

| | | | Parts | | |
|---|---|---|---|---|---|
| Phase | INCI | Trade Name (supplier) | Formulation 1 (Contains gel from example 1) | Formulation 2 (Contains gel from example 3) | Formulation 3 (Comparative) (Contains no elastomer gel) |
| A | Aqua | DI Water | 28.87 | 28.87 | 34.07 |
| | Acrylates/ C10-30 Alkyl Acrylate Crosspoylmer | Carbopol Ultrez 20 (Lubrizol) | 0.08 | 0.08 | 0.08 |
| | Aminomethyl Propanol | AMP-95 (Angus) | 0.07 | 0.07 | 0.07 |
| | Glycerin | Glycerin (Sigma) | 3.60 | 3.60 | 3.60 |
| | Butylene Glycol | Butylene Glycol (Rita) | 0.80 | 0.80 | 0.80 |

TABLE 3-continued

| Phase | INCI | Trade Name (supplier) | Formulation 1 (Contains gel from example 1) | Formulation 2 (Contains gel from example 3) | Formulation 3 (Comparative) (Contains no elastomer gel) |
|---|---|---|---|---|---|
| B | | BELSIL® EG 2 (Wacker Chemie Ag) | 0.00 | 0.00 | 0.00 |
| | | Example 1 gel | 6.00 | 0.00 | 0.00 |
| | | Example 3 gel | 0.00 | 6.00 | 0.00 |
| | Dimethicone | BELSIL® DM 2 (Wacker Chemie Ag) | 0.08 | 0.08 | 0.08 |
| | Polysorbate 20 | Tween 20-LQ-(AP) (Croda) | 0.00 | 0.00 | 0.40 |
| | Polysorbate 80 | Tween 80-LQ-(AP) (Croda) | 0.00 | 0.00 | 0.40 |
| C | CI 59040 | Unicert Green K7157-J (Sensient) | q.s | q.s. | q.s. |
| | Fragrance | Cucumber Mint (Wellington) | q.s. | q.s. | q.s. |
| | Phenoxyethanol (and) Chlorphenesin (and) Decylene Glycol | Microcare PHCD (THOR) | 0.50 | 0.50 | 0.50 |

Procedure:

Disperse Carbopol® Ultrez 20 into water using an Ultra-Turrax® mixer. Add AMP-95 to Phase A and mix with Ultra-Turrax®. Add the rest of Phase A and mix with Ultra-Turrax®. Combine Phase B ingredients in a separate beaker. Add Phase A to Phase B while mixing with Ultra-Turrax®. Add ingredients of Phase C one at a time to the mixture and mix with Ultra-Turrax®.

It was found that no emulsifiers were necessary for Formulations 1 and 2, whereas emulsifiers (Polysorbate 20 and Polysorbate 80) were required to stabilize Formulation 3. This fact shows the benefits of the hydrophilic elastomer gels as emulsifiers.

Evaluation of Formulations

The sensory properties of the Cucumber Moisturizing Gel formulations 1, 2, 3 and 4 were assessed by 8 panelists. For this, the 0.1 g samples were applied on the clean and dry forearm of each panelist while the panelist used one finger to rub the formulation on the forearm. After application on the skin, the sensory properties of the residues were assessed relative to one another. Based on the response of the panelists, the formulations containing hydrophilic elastomer gels (Formulation 1 and Formulation 2) were found to be less tacky and to have better initial and after feel compared to the comparative formulation (Formulation 3) without any of the two hydrophilic gels.

Example in Haircare Formulation: Cleansing Conditioner

Cleansing Conditioner formulations were made with inventive examples 1 (Formulation 4) and 3 (Formulation 5).

TABLE 4

| Phase | INCI | Trade Name (supplier) | Formulation 4 (Contains gel from example 1) | Formulation 5 (Contains gel from example 3) |
|---|---|---|---|---|
| A | Aqua (DI water) | DI Water | 81.40 | 81.40 |
| | Hydroxypropyl starch phosphate | Structure® XL (Essential Ingredients) | 2.00 | 2.00 |
| | Glycerine | BDH Glycerol | 2.00 | 2.00 |

TABLE 4-continued

| Phase | INCI | Trade Name (supplier) | Formulation 4 (Contains gel from example 1) | Formulation 5 (Contains gel from example 3) |
|---|---|---|---|---|
| | Disodium EDTA | Versene ™ NA Disodium EDTA (Dow Chemical) | 0.10 | 0.10 |
| | Cocamidopropyl betaine | Crodateric ™ CAB 30-LQ-(MH) (Croda) | 2.00 | 2.00 |
| B | Cetearyl alcohol | Hallstar ® TA-1618 Cetearyl Alc (Hallstar) | 6.00 | 6.00 |
| | Behentrimonium chloride (and) isopropyl alcohol | BTAC P7580KC (KCI Limited) | 1.80 | 1.80 |
| | Ceteareth-20 | Emulgin ® B2 (BASF) | 1.00 | 1.00 |
| | Polysorbate 80 | Tween ® 80 (Croda) | 0.50 | 0.50 |
| | Sweet almond oil | Sweet Almond Oil (Textron Tecnica) | 0.20 | 0.20 |
| C | | Gel Ex. 1 | 2.00 | |
| | | Gel Ex. 3 | | 2.00 |
| | Phenoxyethanol (and) ethylhexylglycerin | Euxyl ® PE 9010 (Schülke & Mayr GmbH) | 0.50 | 0.50 |
| | Fragrance | Waterlily (Fragrance Resources) | 0.50 | 0.50 |

Procedure:

Add the hydroxypropyl starch phosphate to water while mixing, and mix until completely dissolved. Add the rest of Phase A ingredients individually, then heat mixture to 75° C.

Once the temperature of 75° C. is reached, add each ingredient of Phase B individually, making sure each one is mixed in thoroughly before adding the next. Mix for 5 minutes, then turn off heat and let the mixture to cool down.

Once the temperature is below 40° C., add each of Phase C ingredients individually and mix well in between each addition. Homogenize for additional 5 minutes after all the ingredients have been added.

Example in Color Cosmetics Formulation: 3-in-1 Color Cream 3-in-1 Color Cream formulations were made with inventive examples 1 (Formulation 6) and 3 (Formulation 7).

TABLE 5

| Phase | INCI | Trade Name (supplier) | Formulation 6 (Contains gel from example 1) | Formulation 7 (Contains gel from example 3) |
|---|---|---|---|---|
| A | Glycerin | Glycerol (BDH) | 0.50 | 0.50 |
| | Propylene Glycol | Propylene Glycol USP (Rita) | 0.50 | 0.50 |
| | Disodium EDTA | Versene NA (Dow) | 0.01 | 0.01 |
| | Carbomer | Carbopol Ultrez 21 (Lubrizol) | 0.30 | 0.30 |
| | Aqua | DI Water | 49.10 | 49.10 |
| B | Mineral Oil | Drakeol 21 (Penreco) | 2.00 | 2.00 |
| | C26-28 Alkyl Dimethicone | BELSIL ® CDM 3526 VP (Wacker Chemie AG) | 2.00 | 2.00 |
| | Glyceryl Stearate (and) Benhenyl Alcohol (and) Palmitic Acid | Prolipid 141 (Ashland) | 5.00 | 5.00 |

TABLE 5-continued

| Phase | INCI | Trade Name (supplier) | Formulation 6 (Contains gel from example 1) Parts | Formulation 7 (Contains gel from example 3) Parts |
|---|---|---|---|---|
| | (and) Stearic Acid (and) Lecithin (and) Lauryl Alcohol (and) Myristyl Alcohol (and) Cetyl Alcohol | | | |
| | Ehtylhexyl Palmitate | Rita OP (Rita) | 1.50 | 1.50 |
| | Trimethylsiloxyphenyl Dimethicone | BELSIL ® PDM 1000 (Wacker Chemie AG) | 2.00 | 2.00 |
| C | Cyclopentasiloxane, Caprylyl Dimethicone Ethoxy Glucoside | BELSIL ® SPG 128 VP (Wacker Chemie AG) | 10.00 | 10.00 |
| | Trimethylsiloxysilicate | BELSIL ® TMS 803 (Wacker Chemie AG) | 1.43 | 1.43 |
| | Titanium Dioxide | UF TiO$_2$ (Sensient) | 7.15 | 7.15 |
| | Cl 77491 | Unipure Red LC 381 (Sensient) | 0.70 | 0.70 |
| | Cl 75470 | Unipure Red LC 320 (Sensient) | 0.04 | 0.04 |
| D | | Gel Ex. 1 | 12.00 | |
| | | Gel Ex. 3 | | 12.00 |
| E | Aminomethyl Propanol | AMP-95 (Angus) | 0.27 | 0.27 |
| | Aqua | DI Water | 5.00 | 5.00 |
| F | Propylene Glycol (and) Diazolidinyl Urea (and) Methylparaben (and) Propylparaben | Germaben II (Sutton) | 0.50 | 0.50 |

Procedure:

Using an Ultra-Turrax® mixer, blend Phase C into a paste and set aside. Disperse each ingredient of Phase A, one at a time, into water while stirring. Then heat to 80° C. In a separate beaker, combine Phase B and heat to 80° C. Add Phase C and heat back to 80° C. Once both Phase A and Phase B/C reach 80° C., add Phase B/C into Phase A using the Ultra-Turrax®, Cool down to 50° C., and once temperature reaches 50° C., add Phase D into Phase A/B/C while mixing with the Ultra-Turrax®. Add Phase E and Phase F into Phase A/B/C/D while mixing with the Ultra-Turrax® mixer, and continue mixing until the product is homogenous.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A solvent-swollen, creamy hydrophilic silicone gel composition comprising:
    a crosslinked silicone elastomer containing at least one covalently bonded cyclodextrin moiety, prepared by hydrosilylative crosslinking of reactants (A), (B), and (C)
    (A) optionally, a cyclodextrin reactant comprising a cyclodextrin or cyclodextrin derivative which has been modified to contain an organic group containing aliphatic unsaturation or an organic group containing silicon-bonded hydrogen;
    (B) optionally, an organopolysiloxane having at least one aliphatically unsaturated group;
    wherein reactant (B) is not optional when reactant (A) is not present or where reactant (A) contains no aliphatic unsaturation;
    (C) an organopolysiloxane containing at least one silicon-bonded hydrogen atom,
    the hydrosilylative crosslinking being effected by hydrosilylating aliphatically unsaturated groups of reactant (A), when present, and reactant (B), by means of silicon-bonded hydrogen atoms of reactant (A), when present, and reactant (C), in the presence of a hydrosilylation catalyst (D), wherein at least one cyclodextrin moiety is present among reactants (A), (B), and (C),
    and wherein the hydrosilylative crosslinking is conducted in the presence of a swelling solvent (E), forming a solvent-swollen creamy hydrophilic silicone gel, or wherein the hydrosilylative crosslinking is conducted without swelling solvent and a crosslinked elastomer formed in the hydrosilylative crosslinking is dispersed into a swelling solvent (E) to form a solvent-swollen, creamy hydrophilic silicone gel.

2. The solvent-swollen, creamy hydrophilic silicone gel composition of claim 1, wherein hydrosilylative crosslinking is effected in the presence of swelling solvent (E).

3. The solvent-swollen, creamy hydrophilic silicone gel composition of claim 1, wherein cyclodextrin reactant (A) is present, and comprises cyclodextrin modified to contain at least one aliphatically unsaturated group.

4. The solvent-swollen, creamy hydrophilic silicone gel composition of claim 1, wherein the cyclodextrin reactant (A) is present, and the cyclodextrin reactant contains at least one ether-linked or ester-linked aliphatically unsaturated group.

5. The solvent-swollen, creamy hydrophilic silicone gel composition of claim 1, wherein the cyclodextrin reactant (A) is present, and comprises an ester reaction product of an optionally derivatized cyclodextrin with an organopolysiloxane containing an ester-forming group and at least one aliphatically unsaturated group or with an organopolysiloxane containing an ester-forming group and at least one silicon-bonded hydrogen atom.

6. The solvent-swollen, creamy hydrophilic silicone gel composition of claim 5, wherein the ester-forming group is a carboxylic acid group or a dicarboxylic acid anhydride group.

7. The solvent-swollen, creamy hydrophilic silicone gel composition of claim 1, further comprising one or more guest molecules complexed by cyclodextrin groups of the crosslinked silicon elastomer.

8. The solvent-swollen, creamy hydrophilic silicone gel composition of claim 7, wherein at least one guest molecule is an oxidizable natural oil, a pharmaceutical product, cosmetic active, biocide, insecticide, fungicide, herbicide, pheromone, fragrance, flavoring, pigment, antigen, antistat, flame retardant, UV stabilizer, or dyestuff.

9. The solvent-swollen, creamy hydrophilic silicone gel composition of claim 1, further comprising one or more guest molecules incorporated in the gel inside or outside of cyclodextrin cavity, which can be released at a controlled rate.

10. A process for preparing a solvent-swollen, creamy hydrophilic silicone gel composition of claim 1, comprising mixing reactant (B), reactant (C), hydrosilylation catalyst (D) and optionally reactant (A), optionally in the presence of a swelling solvent, and crosslinking to form a crosslinked silicone elastomer, and if no swelling solvent was present, adding swelling solvent and dispersing the crosslinked silicone elastomer in swelling solvent to form the solvent-swollen, creamy hydrophilic silicone gel composition.

11. A pharmaceutical, personal care, healthcare, woundcare, cosmetic, textile, or coating product, comprising a solvent-swollen, creamy hydrophilic silicone gel composition prepared by the process of claim 10.

12. A pharmaceutical, personal care, healthcare, woundcare, cosmetic, textile, or coating product, comprising a solvent-swollen, creamy hydrophilic silicone gel composition of claim 1.

13. The solvent-swollen, creamy hydrophilic silicone gel of claim 1, comprising from 95 to 30 weight percent of swelling solvent (E).

14. The solvent-swollen, creamy hydrophilic gel of claim 1, wherein the crosslinked silicone elastomer is present in an amount of from 5 to 70 weight percent, based upon the sum of reactants (A), (B), and (C), and swelling solvent (E).

15. The solvent-swollen, creamy hydrophilic silicone gel of claim 1, wherein the swelling solvent comprises a cyclic siloxane.

16. The solvent-swollen, creamy hydrophilic silicone gel of claim 1, wherein the swelling solvent is selected from the group consisting of octamethylcyclotetrasiloxane, decamethylcyclopentasiloxane, volatile oligomeric organopolysiloxanes having 2 to 6 siloxy groups, organopolysiloxane fluids, aliphatic hydrocarbons having 5 carbon atoms or more, cyclohexane, methylcyclohexane, dimethylcyclohexane, lactones, ethylacetate, butyl acetate, hexylacetate and the corresponding propionates and butyrates, alkanol diesters of aliphatic carboxylic acids, and carboxylic diesters of glycols, t-butylmethylether, diethylether, bis(n-propyl carbonate), natural terpene oils, natural fragrance oils, paraffinic oils, natural ester oils, alcohols and glycols having 4-16 carbon atoms, pharmaceutical oils, and mixtures thereof.

17. A solvent-swollen, creamy hydrophilic silicone gel composition of claim 1, which forms a stable aqueous emulsion when added to water.

18. A solvent-swollen, hydrophilic silicone gel composition comprising:
a crosslinked silicone elastomer containing at least one covalently bonded cyclodextrin moiety, prepared by hydrosilylative crosslinking of reactants (A), (B), and (C)
(A) optionally, a cyclodextrin reactant comprising a cyclodextrin or cyclodextrin derivative which has been modified to contain an organic group containing aliphatic unsaturation or an organic group containing silicon-bonded hydrogen;
(B) optionally, an organopolysiloxane having at least one aliphatically unsaturated group;
wherein reactant (B) is not optional when reactant (A) is not present or where reactant (A) contains no aliphatic unsaturation;
(C) an organopolysiloxane containing at least one silicon-bonded hydrogen atom, the hydrosilylative crosslinking being effected by hydrosilylating aliphatically unsaturated groups of reactant (A), when present, and reactant (B), by means of silicon-bonded hydrogen atoms of reactant (A), when present, and reactant (C), in the presence of a hydrosilylation catalyst (D), wherein at least one cyclodextrin moiety is present among reactants (A), (B), and (C),
and wherein the hydrosilylative crosslinking is conducted in the presence of greater than 40 weight percent of a swelling solvent (E), forming a swollen hydrophilic silicone gel, containing said swelling solvent.

19. A solvent-swollen, hydrophilic silicone gel composition of claim 18, wherein the crosslinked silicone elastomer comprises from 5 to 25 weight percent of the solvent-swollen hydrophilic silicone gel, based on the total of the weights of reactants A), B), and C) and swelling solvent E).

20. A solvent-swollen, creamy hydrophilic silicone gel composition of claim 18, which forms a stable aqueous emulsion when added to water.

* * * * *